(12) United States Patent
Desai et al.

(10) Patent No.: US 8,389,525 B2
(45) Date of Patent: Mar. 5, 2013

(54) SMALL MOLECULES FOR INHIBITION OF PROTEIN KINASES

(76) Inventors: Renee Desai, Easton, PA (US); Ketan Desai, Easton, PA (US)

( * ) Notice: Subject to any disclaimer, the term of this patent is extended or adjusted under 35 U.S.C. 154(b) by 271 days.

(21) Appl. No.: 12/774,230

(22) Filed: May 5, 2010

(65) Prior Publication Data

US 2011/0275645 A1 Nov. 10, 2011

(51) Int. Cl.
*A61K 31/498* (2006.01)
*A61K 31/4418* (2006.01)
*C07D 213/85* (2006.01)

(52) U.S. Cl. .................. 514/250; 546/288; 514/344

(58) Field of Classification Search .................. None
See application file for complete search history.

(56) References Cited

FOREIGN PATENT DOCUMENTS

WO 2008008264 A2 1/2008

OTHER PUBLICATIONS

De Leon et al. in Chemistry & Biology 13, 437-441 (2006).*
"RN 831177-52-7" in Database Registry Chemical Abstracts Service, Columbus, Ohio, Accession No. RN 831177-52-7, Entered STN: Feb. 15, 2005.*
Ito et al. in Cancer Science 94(1), 3-8 (2003).*
Bastin et al. in Organic Process Research and Development 2000, 4, 427-435.*
medical-dictionary.thefreedictionary.com/ derivative (downloaded from the internet on Jun. 27, 2012).*
J. G. Cannon Chapter Nineteen in Burger's Medicinal Chemistry and Drug Discovery, Fifth Edition, vol. I: Principles and Practice, Wiley-Interscience 1995, pp. 783-802, 784.*
Rodinovskaya, L., et al., "One-Pot Synthesis of Diverse 4-Di(tri)fluoromethyl-3-cyanopyridine-2(1H)-thiones and Their Utilities in the Cascade Synthesis of Annulated Heterocycles", "J. Comb. Chem.", Feb. 13, 2008, pp. 313-322, vol. 10.
Yuan, Y., et al., "Toward Homogeneous Erythropoietin: Fine Tuning of the C-Terminal Acyl Donor in the Chemical Synthesis of the Cys29-Gly77 Glycopeptide Domain", "J. Am. Chem. Soc.", Mar. 31, 2009, pp. 5432-5437, vol. 131.

* cited by examiner

*Primary Examiner* — Dennis Heyer
(74) *Attorney, Agent, or Firm* — Hultquist, PLLC; David S. Bradin

(57) ABSTRACT

The invention provides compounds that inhibit protein kinases, prodrugs of the compounds, intermediates and methods of synthesizing the compounds and/or prodrugs, pharmaceutical compositions including the compounds and/or prodrugs and methods of using the compounds and/or prodrugs in a variety of contexts, including, for example, in the treatment and/or prevention of various diseases that are responsive to protein kinase inhibition and/or that are mediated, at least in part, by inappropriate kinase activity.

3 Claims, 2 Drawing Sheets

Evaluation of Substrate (poly Glu-Tyr) and Enzyme concentration

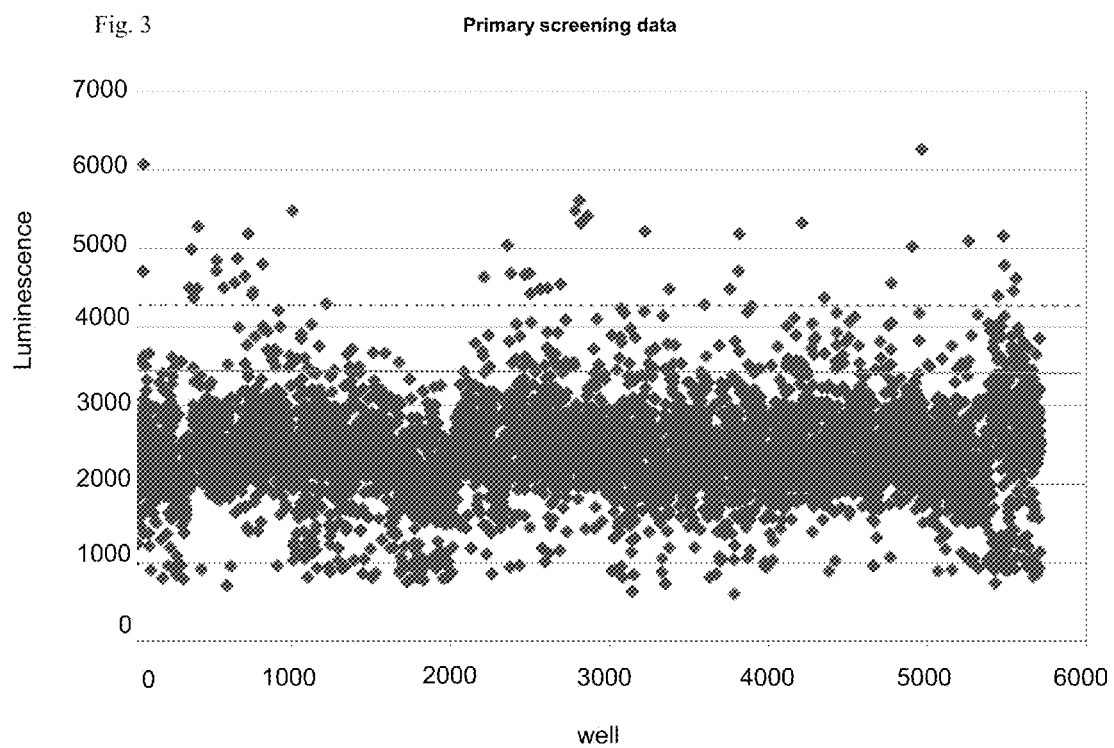

SMALL MOLECULES FOR INHIBITION OF PROTEIN KINASES

BACKGROUND OF THE INVENTION

1. Field of Invention

This invention provides compounds that inhibit protein kinases, prodrugs of the compounds, intermediates and methods of synthesizing the compounds and/or prodrugs, pharmaceutical compositions comprising the compounds and/or prodrugs and methods of using the compounds and/or prodrugs in a variety of contexts, including, for example, in the treatment and/or prevention of various diseases that are responsive to protein kinase inhibition and/or that are mediated, at least in part, by inappropriate kinase activity.

2. Description of Related Art

Protein Kinases

Protein kinases constitute a large family of structurally related enzymes that are responsible for the control of a variety of signal transduction processes within the cell. (See, Hardie, G. and Hanks, S. (1995) The Protein Kinase Facts Book, I and II, Academic Press, San Diego, Calif.). Protein kinases are thought to have evolved from a common ancestral gene due to the conservation of their structure and catalytic function. Almost all kinases contain a similar 250-300 amino acid catalytic domain. The kinases may be categorized into families by the substrates they phosphorylate (e.g., protein-tyrosine, protein-serine/threonine, lipids, etc.). Sequence motifs have been identified that generally correspond to each of these kinase families (See, for example, Hanks, S. K., Hunter, T., FASEB J., 9:576 596 (1995); Knighton et al., Science, 253:407 414 (1991); Hiles et al., Cell, 70:419 429 (1992); Kunz et al., Cell, 73:585 596 (1993); Garcia-Bustos et al., EMBO J., 13:2352 2361 (1994)).

In general, protein kinases mediate intracellular signaling by effecting a phosphoryl transfer from a nucleoside triphosphate to a protein acceptor that is involved in a signaling pathway. These phosphorylation events act as molecular on/off switches that can modulate or regulate the target protein biological function. These phosphorylation events are ultimately triggered in response to a variety of extracellular and other stimuli. Examples of such stimuli include environmental and chemical stress signals (e.g., osmotic shock, heat shock, ultraviolet radiation, bacterial endotoxin, and $H_2O_2$), cytokines (e.g., interleukin-1 (IL-1) and tumor necrosis factor ($\alpha$ TNF-$\alpha$)), and growth factors (e.g., granulocyte macrophage-colony-stimulating factor (GM-CSF), and fibroblast growth factor (FGF)). An extracellular stimulus may affect one or more cellular responses related to cell growth, migration, differentiation, secretion of hormones, activation of transcription factors, muscle contraction, glucose metabolism, control of protein synthesis, and regulation of the cell cycle.

SYK Kinase

Spleen tyrosine kinase (Syk) is a 72-kDa cytoplasmic protein tyrosine kinase that is expressed in a variety of hematopoietic cells and is an essential element in several cascades that couple antigen receptors to cellular responses. Thus, Syk plays a pivotal role in signaling through the Fc receptor and integrins in both neutrophils and macrophages. Syk is also important for signaling of the high affinity IgE receptor, Fc $\epsilon$R1, in mast cells and in receptor antigen signaling in T and B lymphocytes. The signal transduction pathways present in phagocytes, mast, T and B cells have common features. The ligand binding domain of the receptor lacks intrinsic tyrosine kinase activity. However, they interact with transducing subunits that contain immunoreceptor tyrosine based activation motifs (ITAMs) (M. Reth, Nature, 1989, 338, pages 383-384). These motifs are present in both the $\beta$ and $\gamma$ subunits of the Fc $\epsilon$R1, in the $\xi$-subunit the of T cell receptor (TCR) and in the IgG$\alpha$ and IgG$\beta$ subunits of the B cell receptor (BCR) (N. S. van Oers and A. Weiss, Seminars in Immunology, 1995, 7, pages 227-236). Upon binding of antigen and multimerization, the ITAM residues are phosphorylated by protein tyrosine kinases of the Src family. Syk belongs to a unique class of tyrosine kinases that have two tandem Src homology 2 (SH2) domains and a C terminal catalytic domain. These SH2 domains bind with high affinity to ITAMs and this SH2-mediated association of Syk with an activated receptor stimulates Syk kinase activity and localizes Syk to the plasma membrane.

In Syk deficient mice, mast cell degranulation is inhibited, suggesting that this is an important target for the development of mast cell stabilizing agents (P. S. Costello, Oncogene, 1996, 13, pages 2595-2605). Similar studies have demonstrated a critical role for Syk in BCR and TCR signaling (A. M. Cheng, Nature, 1995, 378, pages 303-306, (1995) and D. H. Chu et al., Immunological Reviews, 1998, 165, pages 167-180). Syk also appears to be involved in eosinophil survival in response to IL-5 and GM-CSF (S. Yousefi et al., J. Exp. Med., 1996, 183, pages 1407-1414). Despite the key role of Syk in mast cell, BCR and T cell signaling, little is known about the mechanism by which Syk transmits downstream effectors. Two adaptor proteins, BLNK (B cell Linker protein, SLP-65) and SLP-76 have been shown to be substrates of Syk in B cells and mast cells respectively and have been postulated to interface Syk with downstream effectors (M. Ishiai et al., Immunity, 1999, 10, pages 117-125 and L. R. Hendricks-Taylor et al., J. Biol. Chem, 1997, 272, pages 1363-1367). In addition Syk appears to play an important role in the CD40 signaling pathway, which plays an important role in B cell proliferation (M. Faris et al., J. Exp. Med., 1994, 179, pages 1923-1931).

Syk is further involved in the activation of platelets stimulated via the low-affinity IgG receptor (Fc$\gamma$-RIIA) or stimulated by collagen (F. Yanaga et al., Biochem. J., 1995, 311, (Pt. 2) pages 471-478).

Crosslinking of Fc receptors, such as the high affinity receptors for IgG, IgE (Fc$\epsilon$RI), as well as stimulation through integrins, activates signaling cascades in immune cells that result in the activation of the cells and/or release of preformed mediators. These mediators include molecules such as histamine from mast cells and lactoferrin, catalase, and elastase from neutrophils via degranulation. It also leads to the synthesis and release of other mediators, including cytokines such as TNF alpha and IL 2 as well as nitric oxide, leukotrienes, prostaglandins and platelet-activating factors (PAFs), which play important roles in inflammatory reactions.

The signaling cascade(s) activated by crosslinking Fc receptors such as Fc$\epsilon$RI and/or Fc$\gamma$RI comprises an array of cellular proteins. Among the most important intracellular signal propagators are the tyrosine kinases. And, an important tyrosine kinase involved in the signal transduction pathways associated with crosslinking the Fc$\epsilon$RI and/or Fc$\gamma$RI receptors, as well as other signal transduction cascades, is Syk kinase (see Valent et al., 2002, Intl. J. Hematol. 75(4):357-362 for review). The mediators released as a result of Fc$\epsilon$RI and/or Fc$\gamma$RI receptor cross-linking are responsible for, or play important roles in, the manifestation of numerous events, some of which are adverse. Therefore, there exists a need for compounds which are able to effectively inhibit Syk kinase.

Kinase Diseases

Inappropriately high protein kinase activity has been implicated in many diseases resulting from abnormal cellular function. This might arise either directly or indirectly, for example by failure of the proper control mechanisms for the kinase, related for example to mutation, over-expression or inappropriate activation of the enzyme; or by over- or under-production of cytokines or growth factors also participating in the transduction of signal upstream or downstream of the kinase. In all of these instances, selective inhibition of the action of the kinase might be expected to have a beneficial effect.

Many diseases are associated with abnormal cellular responses triggered by protein kinase-mediated events. These diseases include autoimmune diseases, inflammatory diseases, bone diseases, metabolic diseases, neurological and neurodegenerative diseases, cancer, cardiovascular diseases, allergies and asthma, Alzheimer's disease and hormone-related diseases. Accordingly, there has been a substantial effort in medicinal chemistry to find protein kinase inhibitors that are effective as therapeutic agents. However, considering the lack of currently available treatment options for the majority of the conditions associated with protein kinases, there is still a great need for new therapeutic agents that inhibit these protein targets.

All references cited herein are incorporated herein by reference in their entireties.

BRIEF SUMMARY OF THE INVENTION

Accordingly, a first aspect of the invention comprises a compound selected from the group consisting of:

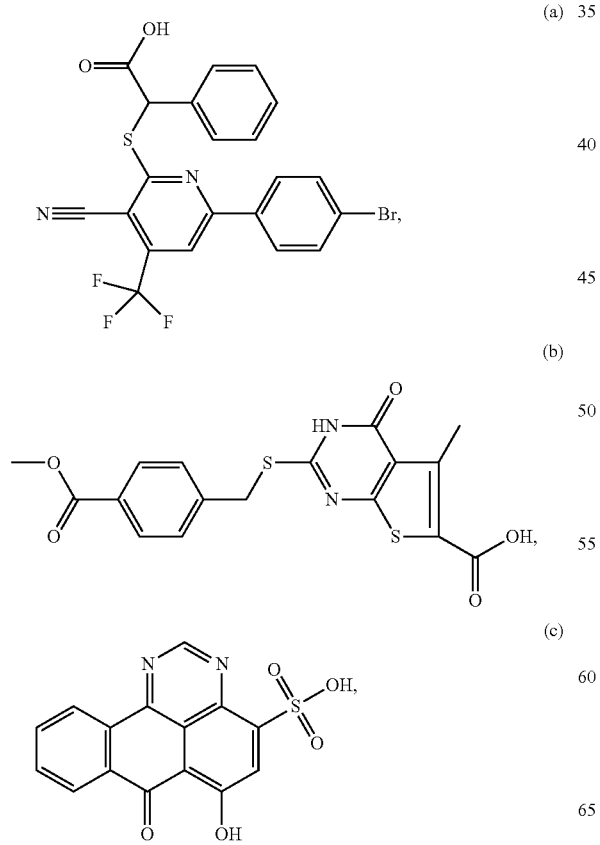

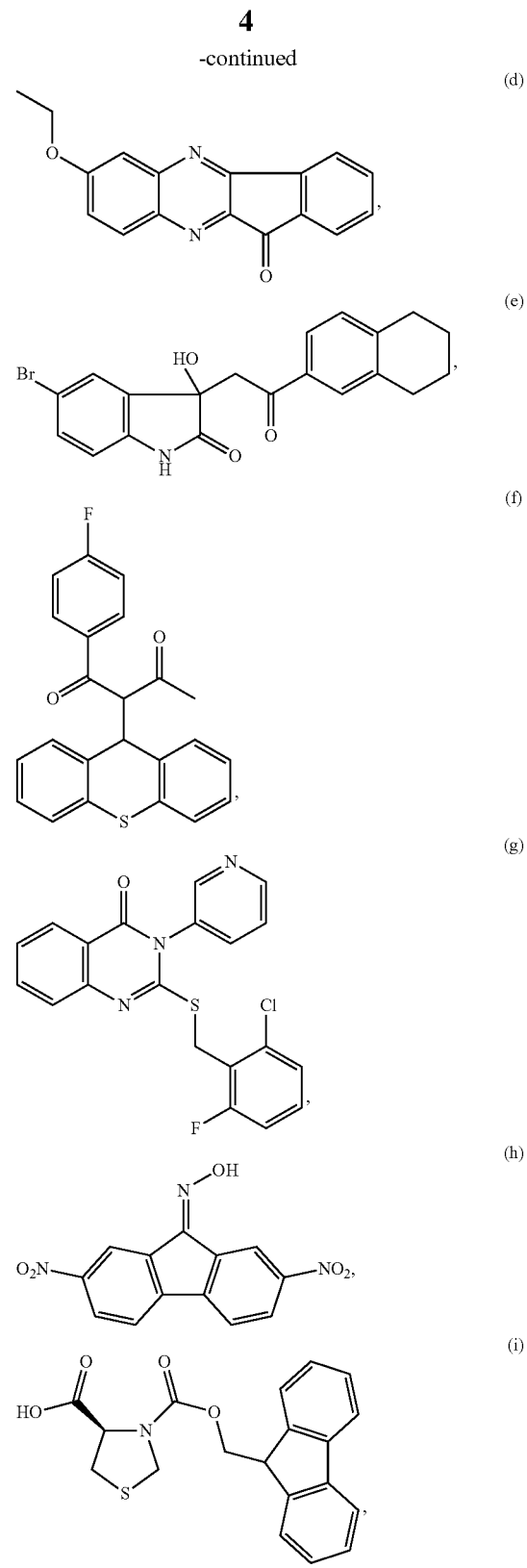

(j) polymorphs thereof, (k) salts thereof, (l) hydrates thereof, (m) solvates thereof and (n) derivatives thereof, wherein the compound is a kinase inhibitor.

A second aspect of the invention comprises a pharmaceutical composition comprising at least one compound of the first aspect of the invention, and at least one of a pharmaceutically acceptable carrier, a diluent and an excipient.

A third aspect of the invention comprises a method of inhibiting a Syk kinase, comprising the step of contacting a Syk kinase or an active fragment thereof with an effective amount of a compound of the first aspect of the invention.

A fourth aspect of the invention comprises a method of inhibiting a Syk kinase in an animal, comprising the step of administering to the animal an amount of a compound of the first aspect of the invention effective to inhibit a Syk kinase.

A fifth aspect of the invention comprises a method of inhibiting an SH2-mediated signal transduction in a mammal in need thereof, which comprises administering to the mammal a compound of the first aspect of the invention in an amount effective to inhibit the SH2-mediated signal transduction.

A sixth aspect of the invention comprises a method of treating a patient who has a proliferative disease, restenosis, osteoporosis, inflammation, allergic reaction, or cardiovascular disease, the method comprising administering to the patient a therapeutically effective amount of a composition of the second aspect of the invention.

A seventh aspect of the invention comprises a method of treating a patient who has a cancer, the method comprising administering to the patient a therapeutically effective amount of a composition of the second aspect of the invention.

An eighth aspect of the invention comprises a method for inducing immunosuppression in a patient, the method comprising administering to the patient an amount of a composition of the second aspect of the invention sufficient to cause immunosuppression.

A ninth aspect of the invention comprises a method of inhibiting a protein kinase comprising contacting a protein kinase with an amount of a compound according to the first aspect of the invention effective to inhibit an activity of the protein kinase.

A tenth aspect of the invention comprises a method of treating, inhibiting, or preventing a kinase-mediated disease, comprising administering to a subject an amount of a compound of the first aspect of the invention effective to treat, inhibit or prevent the kinasemediated disease.

An eleventh aspect of the invention comprises a method of inhibiting FcR or integrin mediated respiratory burst, degranulation or phagocytosis in a cell, said method comprising contacting the cell with an amount of a compound of the first aspect of the invention effective to inhibit FcR or integrin mediated respiratory burst, degranulation or phagocytosis in the cell.

A twelfth aspect of the invention comprises a method of inhibiting IgG-induced or IgE-induced degranulation of a cell, comprising contacting a cell capable of undergoing IgG-induced or IgE-induced degranulation with an amount of a compound of the first aspect of the invention effective to inhibit IgG-induced or IgE-induced degranulation of the cell.

A thirteenth aspect of the invention comprises a method of inhibiting IgG induced or IgE-induced mast or basophil cell degranulation in an animal, comprising administering to the animal an amount of a compound of the first aspect of the invention effective to inhibit IgG-induced or IgE-induced mast or basophil cell degranulation.

BRIEF DESCRIPTION OF THE DRAWINGS

The invention will be described in conjunction with the following drawings, wherein:

FIG. 3 is a graph of luminescence against well number.

DETAILED DESCRIPTION OF PREFERRED EMBODIMENTS OF THE INVENTION

Definitions

Figure 1:
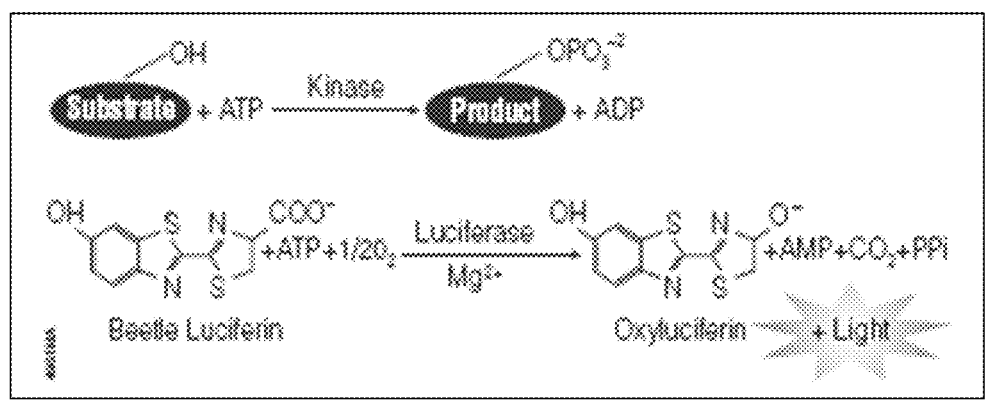
FIG. 1 is a schematic depiction of an assay used to detect activity.

"Kinase-mediated process" or "Kinase-mediated disease or disorder" refers to a cellular process, disease or disorder in which a kinase plays a role. In some embodiments, the kinase is a JAK kinase. The JAK kinases, including JAK3, are abundantly expressed in primary leukemic cells from children with acute lymphoblastic leukemia, the most common form of childhood cancer, and studies have correlated STAT activation in certain cells with signals regulating apoptosis (Demoulin et al., 1996, Mol. Cell. Biol. 16:4710-6; Jurlander et al., 1997, Blood. 89:4146-52; Kaneko et al., 1997, Clin. Exp. Immun. 109:185-193; and Nakamura et al., 1996, J. Biol. Chem. 271:19483-8). They are also known to be important to lymphocyte differentiation, function and survival. JAK-3 in particular plays an essential role in the function of lymphocytes, macrophages, and mast cells. Non-limiting examples of JAK kinase mediated diseases that may be treated or prevented with the compounds, include, but are not limited to allergies, asthma, autoimmune diseases such as transplant rejection (e.g., kidney, heart, lung, liver, pancreas, skin; host versus graft reaction (HVGR), etc), rheumatoid arthritis, and amyotrophic lateral sclerosis, T-cell medicated autoimmune diseases such as multiple sclerosis, psoriasis and Sjogren's syndrome, Type II inflammatory diseases such as vascular inflammation (including vasculitis, arteritis, atherosclerosis and coronary artery disease), diseases of the central nervous system such as stroke, pulmonary diseases such as bronchitis obliteraus and primary pulmonary hypertension, and solid, delayed Type IV hypersensitivity reactions, and hematologic malignancies such as leukemia and lymphomas.

"Therapeutically effective amount" refers to an amount of a compound sufficient to treat a specified disorder or disease by partially or completely alleviating at least one of its symptoms.

"Prophylactically effective amount" refers to an amount of a compound sufficient to prevent or delay the development of a specified disorder or disease. Typically, subjects in which prophylaxis is practiced are not suffering from the specified disorder or disease, but are recognized as being at an elevated risk for developing this disease or disorder based on factors such as, but not limited to, diagnostic markers and family history.

"Syk Kinase" refers to the 72 kDa non-receptor (cytoplasmic) spleen protein tyrosine kinase expressed in hematopoetic cells as well as fibroblasts, epithelial, cells, breast tissue, hepatocytes, neuronal cells and vascular endothelial cells (Yanagi, et al, 2001, 288(3);495-498). Syk kinase includes two consensus Src-homology 2 (SH2) domains in tandem that bind to phosphorylated immunoreceptor tyrosine-based activation motifs ("ITAMs"), a "linker" domain and a catalytic domain (for a review of the structure and function of Syk kinase see Sada et al., 2001, J. Biochem. (Tokyo) 130:177-186); see also Turner et al., 2000, Immunology Today 21:148-154). Syk kinase has been extensively studied as an effector of B-cell receptor (BCR) signaling (Turner et al., 2000, supra). Syk kinase is also critical for tyrosine phosphorylation of multiple proteins that regulate important pathways leading from immunoreceptors, such as $Ca^{2+}$ mobilization and mitogen-activated protein kinase (MAPK) cascades and degranulation. Syk kinase also plays a critical role in integrin signaling in neutrophils (see, e.g., Mocsai et al. 2002, Immunity 16:547558).

As used herein, Syk kinase includes kinases from any species of animal, including but not limited to, homo sapiens, simian, bovine, porcine, rodent, etc., recognized as belonging to the Syk family. Specifically included are isoforms, splice variants, allelic variants, mutants, both naturally occurring and man-made. The amino acid sequences of such Syk kinases are well known and available from GENBANK. Specific examples of mRNAs encoding different isoforms of human Syk kinase can be found at GENBANK Accession No.:

gi|21361552|ref|NM—003177.21;
gi|496899|emb|Z29630.1|HSSYKPTK[496899]; and
gi|5030258|gb|BC011399.11|BC011399[15030258], which are incorporated herein by reference.

Skilled artisans will appreciate that tyrosine kinases belonging to other families may have active sites or binding pockets that are similar in three-dimensional structure to that of Syk. As a consequence of this structural similarity, such kinases, referred to herein as "Syk mimics," are expected to catalyze phosphorylation of substrates phosphorylated by Syk. Thus, it will be appreciated that such Syk mimics, signal transduction cascades in which such Syk mimics play a role, and biological responses effected by such Syk mimics and Syk mimic-dependent signaling cascades may be regulated, and in particular inhibited, with many of the prodrugs described herein.

"Syk-Dependent Signaling Cascade" refers to a signal transduction cascade in which Syk kinase plays a role. Non-limiting examples of such Syk-dependent signaling cascades include the FcαRI, FcεRI, FcγRI, FcγRIII, BCR and integrin signaling cascades.

"Autoimmune Disease" refers to those diseases which are commonly associated with the non-anaphylactic hypersensitivity reactions (Type II, Type III and/or Type IV hypersensitivity reactions) that generally result as a consequence of the subject's own humoral and/or cell-mediated immune response to one or more immunogenic substances of endogenous and/or exogenous origin. Such autoimmune diseases are distinguished from diseases associated with the anaphylactic (Type I or IgE-mediated) hypersensitivity reactions.

"Inflammatory Disease" refers to those diseases which are associated with acute or chronic inflammatory reaction as a response to an endogenous or exogenous stimulus, irrespective of the nature of the stimulus (antigen, hapten, etc). Non-limiting examples of inflammatory disease include asthma, systemic lupus erythematosis, rheumatoid arthritis, gouty arthritis, and the systemic vasculitides.

"Pro-drug" refers to a derivative of an active compound (drug) that may require a transformation under the conditions of use, such as within the body, to release the active drug. Pro-drugs are frequently, but not necessarily, pharmacologically inactive until converted into the active drug. Pro-drugs are typically obtained by masking a functional group in the drug compound believed to be in part required for activity with a pro-group (defined below) to form a pro-moiety which undergoes a transformation, such as cleavage, under the specified conditions of use to release the functional group, and hence the active drug. The cleavage of the pro-moiety may proceed spontaneously, such as by way of a hydrolysis reaction, or it may be catalyzed or induced by another agent, such as by an enzyme, by light, by acid or base, or by a change of or exposure to a physical or environmental parameter, such as a change of temperature. The agent may be endogenous to the conditions of use, such as an enzyme present in the cells to which the pro-drug is administered or the acidic conditions of the stomach, or it may be supplied exogenously.

A wide variety of pro-groups, as well as the resultant pro-moieties, suitable for masking functional groups in the active stereoisomerically enriched compounds described herein to yield pro-drugs are well-known in the art. For example, a hydroxyl functional group may be masked as a sulfonate, ester or carbonate pro-moiety, which may be hydrolyzed in vivo to provide the hydroxyl group. An amino functional group may be masked as an amide, carbamate, imine, urea, phosphenyl, phosphoryl or sulfenyl promoiety, which may be hydrolyzed in vivo to provide the amino group. A carboxyl group may be masked as an ester (including silyl esters and thioesters), amide or hydrazide pro-moiety, which may be hydrolyzed in vivo to provide the carboxyl group. Other specific examples of suitable pro-groups and their respective pro-moieties will be apparent to those of skill in the art.

"Pro-group" refers to a type of protecting group that, when used to mask a functional group within an active stereoisomerically enriched drug compound to form a pro-moiety, converts the drug into a pro-drug. Pro-groups are typically attached to the functional group of the drug via bonds that are cleavable under specified conditions of use. Thus, a pro-group is that portion of a pro-moiety that cleaves to release the functional group under the specified conditions of use. As a specific example, an amide pro-moiety of the formula —NH—C(O)CH$_3$ comprises the pro-group —C(O)CH$_3$.

The Compounds

A first aspect of the invention encompasses compounds that have useful biological activities, including the ability to inhibit a variety of protein kinases, for example, SYK kinase, in vitro and/or in vivo. The compounds of the invention are grouped into the nine different classes described below.

Class 1: Compound 1 and Structural Analogs thereof

Compound 1 is α-[[6-(4-bromophenyl)-3-cyano-4-(trifluoromethyl)-2-pyridinyl]thio]-benzeneacetic acid, having the CAS Reg. No. 625369-82-6, and the structure shown below.

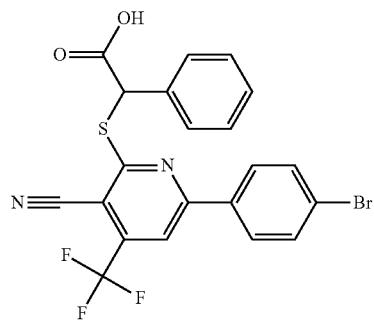

Structure
Formula C$_{21}$H$_{12}$BrF$_3$N$_2$O$_2$S
Molweight 493.2963896

Rodinovskaya et al., "One-Pot Synthesis of Diverse 4-Di(tri)fluoromethyl-3-cyanopyridine-2(1H)-thiones and Their Utilities in the Cascade Synthesis of Annulated Heterocycles." J. Comb. Chem, 2008, 10, (2), pp 313-322 discloses a method for synthesizing Compound 1 and structural analogs thereof.

WO 2007124545 A1 discloses the preparation of structural analogs of Compound 1 for use as integrase inhibitors, including (3-cyano-6-phenyl-4-trifluoromethylpyridin-2-ylsulfanyl)-phenyl-acetic acid (aka α[[3-cyano-6-phenyl-4-(trifluoromethyl)-2-pyridinyl]thio]-benzeneacetic acid) at page 46, which differs from Compound 1 only in the absence of a bromine substituent on the 6-phenyl group.

Class 2: Compound 2 and Structural Analogs thereof

Compound 2 is 1,4-dihydro-2-[[[4-(methoxycarbonyl)phenyl]methyl]thio]-5-methyl-4-oxo-thieno-[2,3-d]pyrimidine-6-carboxylic acid, having the CAS Reg. No. 831177-52-7 and the structure shown below.

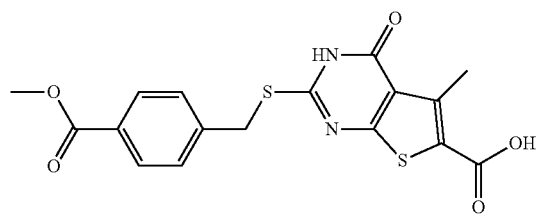

Structure
Formula $C_{17}H_{14}N_2O_5S_2$
Molweight 390.43346

Compound 2 can be synthesized in accordance with the following reaction equation.

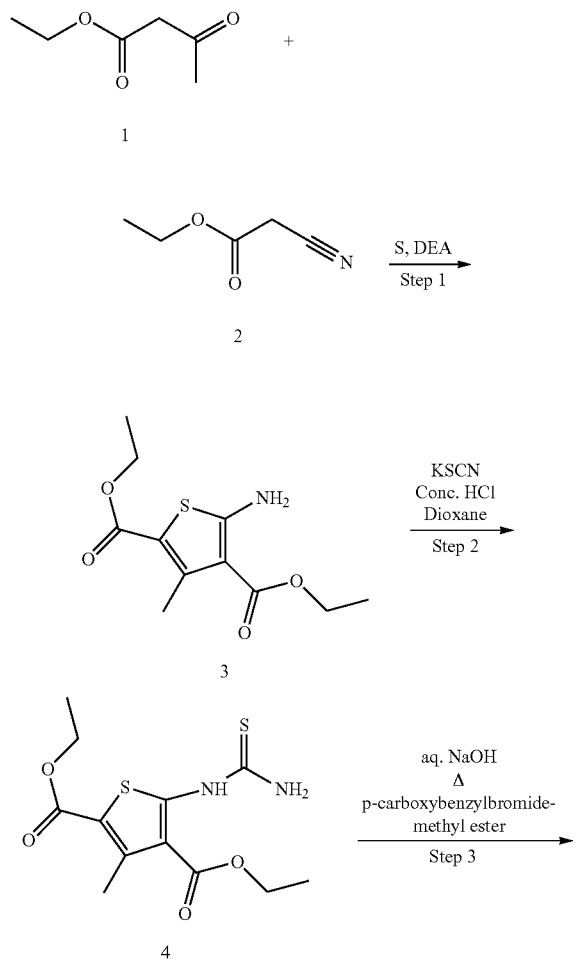

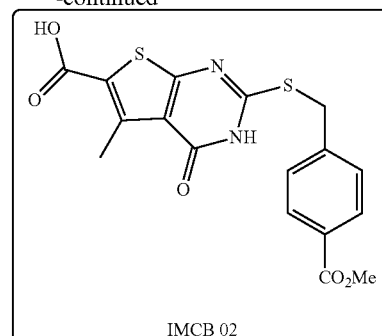

IMCB 02

WO2008045406 discloses structural analogs of Compound 2 having the Formula (I):

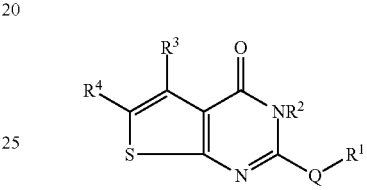

I where Q=—S—, —S(O)—, and —S(O)2-; R1=C1-C9 alkyl, C2-C9 alkyenyl, C2-C9 alkynyl, C6-C12 aryl, and C1-C12 carbonyl; R2=C1-C9 alkaryl, and C6-C12 aryl; and R3 and R4 are independently C1-C9 alkyl, C2-C9 alkenyl, C2-C9 alkynyl, C1-C9 alkyloxy, and C1-C12 carbonyl, or R3 and R4, combined, form an C3-C9 carbocyclic, C2-C9 heterocyclic, C6-C12 aryl, or C2-C12 heteroaryl, ring system), pharmaceutical compounds, methods of synthesis, and methods for treating diseases and conditions associated with cellular necrosis.

Ivachtchenko et al., "Synthesis of Substituted Thienopyrimidine-4-ones" J. Combinatorial Chem. (2004), 6(4), 573-583, discloses methods for synthesizing structural analogs of Compound 2.

Class 3: Compound 3 and Structural Analogs thereof

Compound 3 is 6-hydroxy-7-oxo-7H-benzo[e]perimidine-4-sulfonic acid, having the CAS Reg. No. 293326-43-9 and the structure shown below.

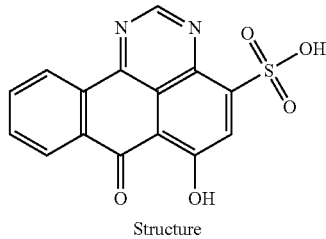

Structure
Formula $C_{15}H_8N_2O_5S$
Molweight 328.29942

De Leon et al., "An In Vitro Screen of Bacterial Lipopolysaccharide Biosynthetic Enzymes Identifies an Inhibitor of ADP-Heptose Biosynthesis." Chem & Biol (2006), 13(4), 437-441, discloses 6-hydroxy-7H-benzo[e]perimidin-7-one, a structural analog of Compound 3.

PL 180370 and U.S. Pat. Nos. 2,032,772 and 3,862,944 disclose the structurally related class of compounds known as hydroxyanthrapyrimidines and methods of synthesizing them.

Class 4: Compound 4 and Structural Analogs thereof

Compound 4 is 7-ethoxy-11H-indeno[1,2-b]quinoxalin-11-one, having the CAS Reg. No. 328977-60-2 and the structure shown below.

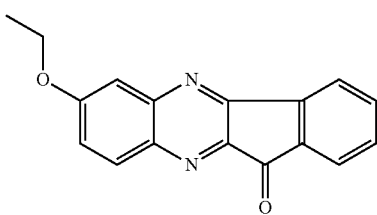

Structure
Formula $C_{17}H_{12}N_2O_2$
Molweight 276.28938

U.S. Pat. No. 5,789,427 to Chen et al. discloses structurally analogous compounds, 11H-Indeno[1,2-b]quinoxalin-11-ones, useful as tyrosine kinase inhibitors. No mention of its effect on syk was noted.

Class 5: Compound 5 and Structural Analogs thereof

Compound 5 is 5-bromo-1,3-dihydro-3-hydroxy-3-[2-oxo-2-(5,6,7,8-tetrahydro-2-naphthalenyl)ethyl]-2H-indol-2-one, having the CAS Reg. No. 362506-63-6 and the structure shown below.

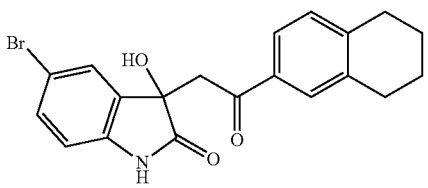

Structure
Formula $C_{20}H_{18}BrNO_3$
Molweight 400.26582

Class 6: Compound 6 and Structural Analogs thereof

Compound 6 is 1-(4-fluorophenyl)-2-(9H-thioxanthen-9-yl)-1,3-butanedione, having the CAS Reg. No. 433697-23-5 and the structure shown below.

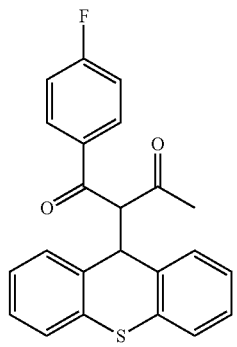

Structure
Formula $C_{23}H_{17}FO_2S$
Molweight 376.4432832

Sawicki et al., "Reaction of thiaxanthydrol with compounds containing active hydrogen." Journal of Organic Chemistry (1956), 21, 183-9 discloses structural analogs of Compound 6 and methods for preparing them.

Class 7: Compound 7 and Structural Analogs thereof

Compound 7 is 2-[[(2-chloro-6-fluorophenyl)methyl]thio]-3-(3-pyridinyl)-4(3H)-quinazolinone, having the CAS Reg. No. 215654-80-1 and the structure shown below.

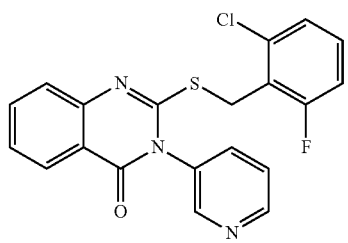

Structure
Formula $C_{20}H_{13}ClFN_3OS$
Molweight 397.8531232

DD 255531 discloses structural analogs said to be useful as vasodilators and sedatives, including:

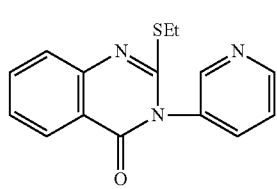

Compound 7 can be synthesized in accordance with the following reaction equation.

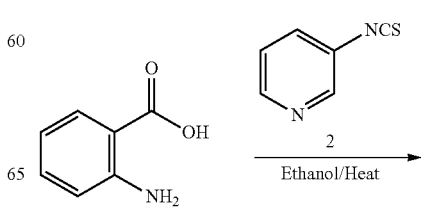

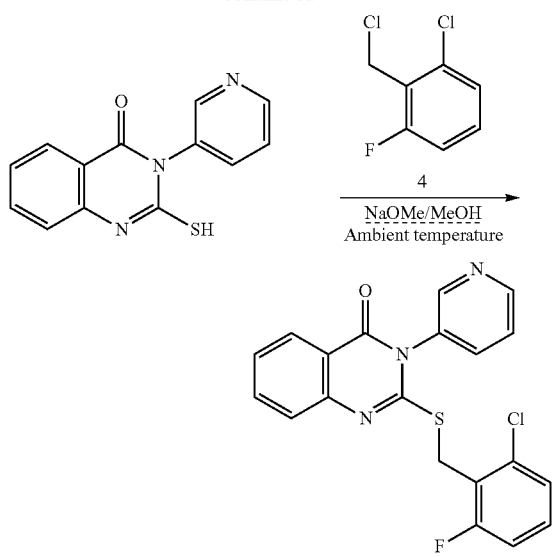

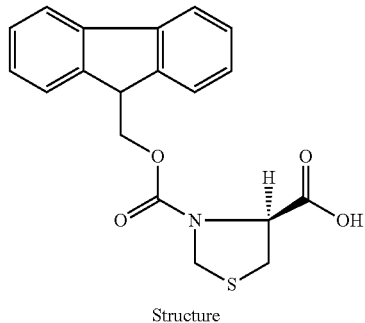

Structure
Formula $C_{19}H_{17}NO_4S$
Molweight 355.40758

WO 2002038591 discloses Compound 9 as a prodrug capable of being converted into a cytotoxic or cytostatic drug by fibroblast activation protein.

Compound 9 can be synthesized in accordance with the following reaction equation.

Class 8: Compound 8 and Structural Analogs thereof

Compound 8 is 2,7-dinitro-oxime-9H-fluoren-9-one, having the CAS Reg. No 23818259 and the structure shown below.

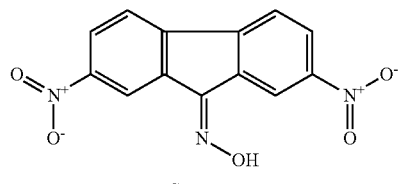

Structure
Formula $C_{13}H_7N_3O_5$
Molweight 285.21178

WO 2007016338 discloses Compound 8 as a Chk2 kinase inhibitor compound although it was not tested against Syk.

Compound 8 can be synthesized in accordance with the following reaction equation.

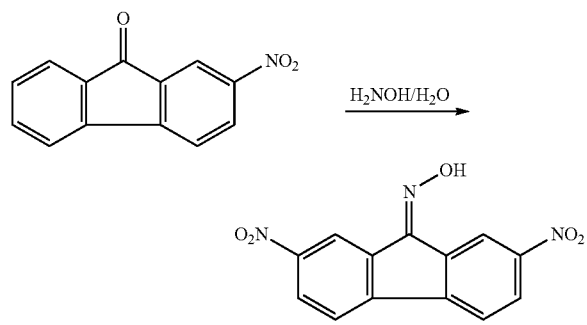

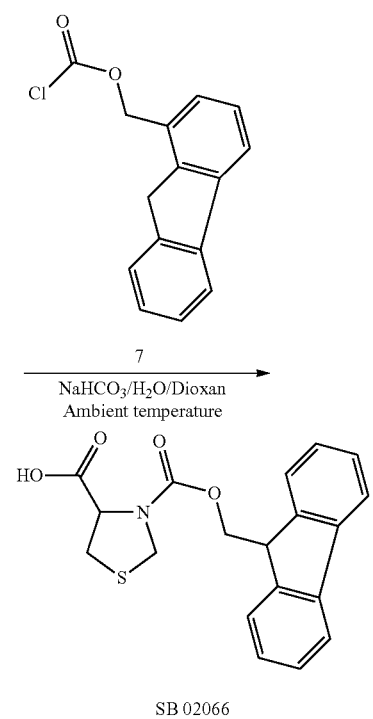

SB 02066

Class 9: Compound 9 and Structural Analogs thereof

Compound 9 is 3-(9H-fluoren-9-ylmethyl) ester-3,4-thiazolidinedicarboxylic acid, having the CAS Reg. No 423719-54-4 and the structure shown below.

Pharmaceutical Dosages and Administration

The compounds may be administered per se in the form of prodrugs or as pharmaceutical compositions, comprising an active compound or pro-drug. Pharmaceutical compositions comprising the active compounds (or prodrugs thereof) may be manufactured by means of conventional mixing, dissolving, granulating, dragee-making, levigating, emulsifying, encapsulating, entrapping or lyophilization processes. The compositions may be formulated in conventional manner using one or more physiologically acceptable carriers, diluents, excipients or auxiliaries which facilitate processing of the active compounds into preparations which can be used pharmaceutically (see Remington's Pharmaceutical Sciences, 15th Ed., Hoover, J. E. ed., Mack Publishing Co. (2003).

The active compound or pro-drug may be formulated in the pharmaceutical compositions per se, or in the form of a hydrate, solvate, N-oxide or pharmaceutically acceptable salt, as previously described. Typically, such salts are more soluble in aqueous solutions than the corresponding free acids and bases, but salts having lower solubility than the corresponding free acids and bases may also be formed.

Pharmaceutical compositions may take a form suitable for virtually any mode of administration, including, for example, topical, ocular, oral, buccal, systemic, nasal, intramuscular, transdermal, rectal, vaginal, etc., or a form suitable for administration by inhalation or insufflation.

For topical administration, the active compound(s) or pro-drug(s) may be formulated as solutions, gels, ointments, creams, suspensions, etc. as are well-known in the art.

Systemic formulations include those designed for administration by injection, e.g., subcutaneous, intravenous, intramuscular, intrathecal or intraperitoneal injection, as well as those designed for transdermal, transmucosal, oral or pulmonary administration.

Useful injectable preparations include sterile suspensions, solutions or emulsions of the active compound(s) in aqueous or oily vehicles. The compositions may also contain formulating agents, such as suspending, stabilizing and/or dispersing agent. The formulations for injection may be presented in unit dosage form, e.g., in ampoules or in multidose containers, and may contain added preservatives.

Alternatively, the injectable formulation may be provided in powder form for reconstitution with a suitable vehicle, including but not limited to sterile pyrogen free water, buffer, dextrose solution, etc., before use. To this end, the active compound(s) may be dried by any art-known technique, such as lyophilization, and reconstituted prior to use.

For transmucosal administration, penetrants appropriate to the barrier to be permeated are used in the formulation. Such penetrants are known in the art.

For oral administration, the pharmaceutical compositions may take the form of, for example, lozenges, tablets, films or capsules prepared by conventional means with pharmaceutically acceptable excipients such as binding agents (e.g., pregelatinized maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulfate, lecithin). The tablets may be coated by methods well known in the art with, for example, sugars, films or enteric coatings.

Liquid preparations for oral administration may take the form of, for example, elixirs, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol, CREMOPHORE® or fractionated vegetable oils); and preservatives (e.g., methyl or propyl-p-hydroxybenzoates or sorbic acid). The preparations may also contain buffer salts, preservatives, flavoring, coloring and sweetening agents as appropriate.

Preparations for oral administration may be suitably formulated to give controlled release of the active compound or pro-drug, as is well known in the art.

For buccal administration, the compositions may take the form of tablets or lozenges formulated in conventional manner.

For rectal and vaginal routes of administration, the active compound(s) may be formulated as solutions (for retention enemas) suppositories or ointments containing conventional suppository bases such as cocoa butter or other glycerides.

For nasal administration or administration by inhalation or insufflation, the active compound(s) or pro-drug(s) can be conveniently delivered in the form of an aerosol spray from pressurized packs or a nebulizer with the use of a suitable propellant, e.g., dichlorodifluoromethane, trichlorofluoromethane, dichlorotetrafluoroethane, fluorocarbons, carbon dioxide or other suitable gas. In the case of a pressurized aerosol, the dosage unit may be determined by providing a valve to deliver a metered amount. Capsules and cartridges for use in an inhaler or insufflator (for example capsules and cartridges comprised of gelatin) may be formulated containing a powder mix of the compound and a suitable powder base such as lactose or starch.

For ocular administration, the active compound(s) or pro-drug(s) may be formulated as a solution, emulsion, suspension, etc. suitable for administration to the eye. A variety of vehicles suitable for administering compounds to the eye are known in the art. Specific non-limiting examples are described in U.S. Pat. Nos. 6,261,547; 6,197,934; 6,056,950; 5,800,807; 5,776,445; 5,698,219; 5,521,222; 5,403,841; 5,077,033; 4,882,150; and 4,738,851.

For prolonged delivery, the active compound(s) or pro-drug(s) can be formulated as a depot preparation for administration by implantation or intramuscular injection. The active ingredient may be formulated with suitable polymeric or hydrophobic materials (e.g., as an emulsion in an acceptable oil) or ion exchange resins, or as sparingly soluble derivatives, e.g., as a sparingly soluble salt. Alternatively, transdermal delivery systems manufactured as an adhesive disc or patch which slowly releases the active compound(s) for percutaneous absorption may be used. To this end, permeation enhancers may be used to facilitate transdermal penetration of the active compound(s). Suitable transdermal patches are described in for example, U.S. Pat. Nos. 5,407, 713; 5,352,456; 5,332,213; 5,336,168; 5,290,561; 5,254,346; 5,164,189; 5,163,899; 5,088,977; 5,087,240; 5,008,110; and 4,921,475.

Alternatively, other pharmaceutical delivery systems may be employed. Liposomes and emulsions are well-known examples of delivery vehicles that may be used to deliver active compound(s) or pro-drug(s). Certain organic solvents such as dimethylsulfoxide (DMSO) or other vehicles such as CREMOPHOR® (a class of non-ionic solubilizers and emulsifiers manufactured by BASF Corporation, Florham Park, N.J.), may also be employed, although usually at the cost of greater toxicity.

The pharmaceutical compositions may, if desired, be presented in a pack or dispenser device that may contain one or more unit dosage forms containing the active compound(s). The pack may, for example, comprise metal or plastic foil, such as a blister pack. The pack or dispenser device may be accompanied by instructions for administration.

Effective Dosages

The active compound(s) or pro-drug(s), or compositions thereof, will generally be used in an amount effective to achieve the intended result, for example in an amount effective to treat or prevent the particular disease being treated. The compound(s) may be administered therapeutically to achieve therapeutic benefit. By therapeutic benefit is meant eradication or amelioration of the underlying disorder being treated and/or eradication or amelioration of one or more of the symptoms associated with the underlying disorder such that the patient reports an improvement in feeling or condition, notwithstanding that the patient may still be afflicted with the underlying disorder. Therapeutic benefit also includes halting or slowing the progression of the disease, regardless of whether improvement is realized.

For example, administration of a compound to a patient suffering from an allergy provides therapeutic benefit not only when the underlying allergic response is eradicated or ameliorated, but also when the patient reports a decrease in the severity or duration of the symptoms associated with the allergy following exposure to the allergen. As another example, therapeutic benefit in the context of asthma includes an improvement in respiration following the onset of an asthmatic attack, or a reduction in the frequency or severity of asthmatic episodes. As another specific example, therapeutic benefit in the context of transplantation rejection includes the ability to alleviate an acute rejection episode, such as, for example, the HVGR (host versus graft response), or the ability to prolong the time period between onset of acute rejection episodes and/or onset of chronic rejection. Therapeutic benefit also includes halting or slowing the progression of the disease, regardless of whether improvement is realized.

For prophylactic administration, the compound may be administered to a patient at risk of developing one of the previously described conditions. For example, if it is unknown whether a patient is allergic to a particular drug, the compound may be administered prior to administration of the drug to avoid or ameliorate an allergic response to the drug. Alternatively, prophylactic administration may be applied to avoid the onset of symptoms in a patient diagnosed with the underlying disorder. For example, a compound may be administered to an allergy sufferer prior to expected exposure to the allergen. Compounds may also be administered prophylactically to healthy individuals who are repeatedly exposed to agents known to induce one of the above-described maladies to prevent the onset of the disorder. For example, a compound may be administered to a healthy individual who is repeatedly exposed to an allergen known to induce allergies, such as latex, in an effort to prevent the individual from developing an allergy: Alternatively, a compound may be administered to a patient suffering from asthma prior to partaking in activities that trigger asthma attacks to lessen the severity of, or avoid altogether, an asthmatic episode.

In the context of transplant rejection, the compound may be administered while the patient is not having an acute rejection reaction to avoid the onset of rejection and/or prior to the appearance of clinical indications of chronic rejection.

The amount of compound administered will depend upon a variety of factors, including, for example, the particular indication being treated, the mode of administration, the severity of the indication being treated and the age and weight of the patient, the bioavailability of the particular active compound, etc. Determination of an effective dosage is well within the capabilities of those skilled in the art.

As known by those of skill in the art, the preferred dosage of the compounds will also depend on the age, weight, general health and severity of the condition of the individual being treated. Dosage may also need to be tailored to the sex of the individual and/or where administered by inhalation, the lung capacity of the individual. Dosage may also be tailored to individuals suffering from more than one condition or those individuals who have additional conditions which affect lung capacity and the ability to breathe normally, for example, emphysema, bronchitis, pneumonia, respiratory infections, etc. Dosage, and frequency of administration of the compounds or prodrugs thereof, will also depend on whether the compounds are formulated for treatment of acute episodes of a condition or for the prophylactic treatment of a disorder. For example, acute episodes of allergic conditions, including allergy-related asthma, transplant rejection, etc. A skilled practitioner will be able to determine the optimal dose for a particular individual.

Effective dosages may be estimated initially from in vitro assays. For example, an initial dosage for use in animals may be formulated to achieve a circulating blood or serum concentration of active compound that is at or above an IC 50 of the particular compound as measured in an in vitro assay, such as the in vitro assays described in the Examples section. Calculating dosages to achieve such circulating blood or serum concentrations taking into account the bioavailability of the particular compound is well within the capabilities of skilled artisans. For guidance, the reader is referred to Fingl & Woodbury, "General Principles," In: Goodman and Gilman's The Pharmaceutical Basis of Therapeutics, latest edition, supra, and the references cited therein.

Initial dosages may also be estimated from in vivo data, such as animal models.

Animal models useful for testing the efficacy of compounds to treat or prevent the various diseases described above are well-known in the art. Suitable animal models of hypersensitivity or allergic reactions are described in Foster, 1995, Allergy 50(21Suppl):6-9, discussion 34-38 and Tumas et al., 2001, J. Allergy Clin. Immunol. 107(6):1025-1033. Suitable animal models of allergic rhinitis are described in Szelenyi et al:, 2000, Arzneimittelforschung 50(11):1037-42; Kawaguchi et al., 1994, Clin. Exp. Allergy 24(3):238-244 and Sugimoto et al., 2000, Immunopharmacology 48(1):1-7. Suitable animal models of allergic conjunctivitis are described in Carreras et al., 1993, Br. J. Ophthalmol. 77(8): 509-514; Saiga et al., 1992, Ophthalmic Res. 24(1):45-50; and Kunert et al., 2001, Invest. Ophthalmol. Vis. Sci. 42(11): 2483-2489. Suitable animal models of systemic mastocytosis are described in O'Keefe et al., 1987, J. Vet. Intern. Med. 1(2):75-80 and Bean-Knudsen et al., 1989, Vet. Pathol. 26(1): 90-92. Suitable animal models of hyper IgE syndrome are described in Claman et al., 1990, Clin. Immunol. Immunopathol. 56(1):46-53. Suitable animal models of B-cell lymphoma are described in Hough et al., 1998, Proc. Natl. Acad. Sci. USA 95:13853-13858 and Hakim et al., 1996, J. Immunol. 157(12):5503-55 11. Suitable animal models of atopic disorders such as atopic dermatitis, atopic eczema and atopic asthma are described in Chan et al., 2001, J. Invest. Dermatol. 117(4):977-983 and Suto et al., 1999, Int. Arch. Allergy Immunol. 120(Suppl 1):70-75. Suitable animal models of transplant rejection, such as models of the HVGR are described in O'Shea et al., 2004, Nature Reviews Drug Discovery 3:555-564; Cetkovic-Curlje & Tibbles, 2004, Current Pharmaceutical Design 10:1767-1784; and Chengelian et al., 2003, Science 302:875-878. Suitable animal models of vasculitis are described in Pelletier et al., 1987 Nephrol Dial Transplant 1:211-218, Mathieson et al., 1992 Lab Invest. 67:121-129, and Xiao et al., 2002, J. Clin Invest 110:955. A suitable animal model for gout is described in Getting et al., 1997, J Pharmacol. Exp. Ther. 283:123. A suitable model for lupus is described in Bielschowsky et al, 1959, Proc. Univ. Otago Med School 37:9 and Monneaux et al, 2001, International Immunology 13(9):1155-1163. A suitable model for rheumatoid arthritis is described in Cope, 2007, Arthritis Research: Methods and Protocos, Springer, p191-215 and Knight et al, 1992, Clin Exp Immnol 20(3):459-465. Ordinarily skilled artisans can routinely adapt such information to determine dosages suitable for human administration.

Dosage amounts will typically be in the range of from about 0.0001 or 0.001 or 0.01 mg/kg/day to about 100 mg/kg/day, but may be higher or lower, depending upon, among other factors, the activity of the compound, its bioavailability, the mode of administration and various factors discussed above. Dosage amount and interval may be adjusted individually to provide plasma levels of the compound(s) that are sufficient to maintain therapeutic or prophylactic effect. For example, the compounds may be administered once per week, several times per week (e.g., every other day), once per day or multiple times per day, depending upon, among other things, the mode of administration, the specific indication being treated and the judgment of the prescribing physician. In cases of local administration or selective uptake, such as local topical administration, the effective local concentration of active compound(s) may not be related to plasma concentration. Skilled artisans will be able to optimize effective local dosages without undue experimentation.

Preferably, the compound(s) will provide therapeutic or prophylactic benefit without causing substantial toxicity. Toxicity of the compound(s) may be determined using standard pharmaceutical procedures. The dose ratio between toxic and therapeutic (or prophylactic) LD 50/ED 50 effect is the therapeutic index (LD 50 is the dose lethal to 50% of the population and ED 50 is the dose therapeutically effective in 50% of the population). Compounds(s) that exhibit high therapeutic indices are preferred.

Kits

The compounds and/or prodrugs described herein may be assembled in the form of kits. In some embodiments, the kit provides the compound(s) and reagents to prepare a composition for administration. The composition may be in a dry or lyophilized form, or in a solution, particularly a sterile solution. When the composition is in a dry form, the reagent may comprise a pharmaceutically acceptable diluent for preparing a liquid formulation. The kit may contain a device for administration or for dispensing the compositions, including, but not limited to syringe, pipette, transdermal patch, or inhalant.

The kits may include other therapeutic compounds for use in conjunction with the compounds described herein. In some embodiments, the therapeutic agents are other anti-cancer and anti-neoplastic compounds. These compounds may be provided in a separate form, or mixed with the compounds of the present invention.

The kits will include appropriate instructions for preparation and administration of the composition, side effects of the compositions, and any other relevant information. The instructions may be in any suitable format, including, but not limited to, printed matter, videotape, computer readable disk, or optical disc.

Uses of Compounds and Pharmaceutically Acceptable Compositions

The compounds and compositions described herein are generally useful for the inhibition of kinase activity of one or more enzymes. Kinases include, for example, protein kinases, lipid kinases (e.g., phosphatidylinositol kinases PI-3, PI-4) and carbohyhdrate kinases. Further information relating to kinase structure, function and their role in disease or disease symptoms is available at the Protein Kinase Resource website (http://Ikinases.sdsc.edu/html/index.shtml).

It will be appreciated that compounds described herein are preferably useful as inhibitors of Syk, though they may also inhibit tyrosine, serine/threonine or histidine protein kinases. Examples of kinases that may be inhibited by the compounds and compositions described herein and against which the methods described herein are useful include, but are not limited to, SYK, LCK, IRK (=INSR=Insulin receptor), IGF-1 receptor, MK2, ZAP-70, Aurora-2, PRAK, ROCK, CAK, cMET, IRAK1, IRAK2, BLK, BMX, BTK, FRK, FGR, FYN, HCK, ITK, LYN, TEC, TXK, YES, ABL, SRC, EGF-R (=ErbB-1), ErbB-2 (=NEU=HER 2), ErbB-3, ErbB-4, FAK, FGF1R (=FGR-1), FGF2R (=FGR-2), IKK-1 (=IKK-α=CHUK), IKK-2 (=HOC-β), MET (=c-Met), NIK, PGDF receptor α, PDGF receptor β, TIE1, TIE2 (=TEK), VEGFR 1 (=FLT-1), VEGFR 2 (=KDR), FLT-3, FLT-4, KIT, CSK, JAK1, JAK2, JAK3, TYK2, RIP, RIP-2, LOK, TAKI, RET, ALK, MLK3, COT, TRKA, PYK2, EPHB4, RON, GSK3, UL13, ORF47, ATM, CDK (including all subtypes), PKA, PKB (including all PKB subtypes) (=AKT-1, AKT-2, AKT-3), PKC (including all PKC subtypes), REDK, SAPK, PIM, PDK, PIM, ERK and BARK, and all subtypes of these kinases. The compounds and compositions of the invention are therefore also particularly suited for the treatment of diseases and disease symptoms that involve one or more of the aforementioned kinases.

The compounds described herein inhibit protein kinases in in vitro assays. Thus, in still another aspect of the invention, methods of inhibiting protein kinases are provided. The methods generally involve contacting a protein kinase with an amount of one or more compounds described herein, and/or prodrugs, salts, hydrates, solvates and/or N-oxides thereof, effective to inhibit its activity. The methods may be practiced in in vitro contexts, or in in vivo contexts as a therapeutic approach towards the treatment or prevention of disorders responsive to protein kinase inhibition. Protein kinases that can be inhibited with the compounds desired herein include, but are not limited Syk, JAK1, JAK3, Ax1, Lck and Lyn Kinases.

In still another aspect of the invention, methods of treating, inhibiting, and/or preventing diseases that are responsive to protein kinase inhibition, or in which inappropriate protein kinase activity plays a role, are provided. The methods may be practiced in animals in veterinary contexts and/or in humans. The methods generally involve administering to an animal or human subject an amount of one or more compounds described herein, and/or prodrugs, salts, hydrates, solvates and/or N-oxides thereof, effective to treat and/or prevent the particular disease. The compound(s) per se can be administered to the subject, or the compound(s) can be administered in the form of a composition. Diseases and other conditions that are responsive to protein kinase inhibition, and/or that are believed to be effected, at least in part, by inappropriate protein kinase activity, that can be treated, inhibited, and/or prevented according to the methods include, but are not limited to: autoimmune diseases, such as vasculitis, rheumatoid arthritis, multiple sclerosis, and systemic lupus erythematosus; transplant rejection; graft-versus-host disease; hyperproliferative disorders, such as tumors, psoriasis; pannus formation in rheumatoid arthritis; restenosis following angioplasty and atherosclerosis, osteoporosis; and diseases in which cells receive pro-inflammatory signals, such as asthma, inflammatory bowel disease and pancreatitis. Metabolic diseases that have an inflammatory component (such as gout) would also be responsive to these drugs.

In particular, inhibition of Syk and/or Lyn kinase would be expected to be useful in treating, inhibiting, and/or preventing diseases that are characterized by, caused by and/or associated with the IgE receptor signaling cascade, which leads to degranulation of immune cells such as mast cells, and the consequent release of mediators of inflammation. Such diseases include, by way of example and not limitation, atopy or anaphylactic hypersensitivity or allergic reactions, allergies (e.g., allergic conjunctivitis, allergic rhinitis, atopic asthma, atopic dermatitis and food allergies), low grade scarring (e.g., of scleroderma, increased fibrosis, keloids, post-surgical scars, pulmonary fibrosis, vascular spasms, migraine, reperfusion injury and post myocardial infarction), diseases associated with tissue destruction (e.g., chronic obstructive pulmonary disease), diseases associated with tissue inflammation (e.g., irritable bowel syndrome, spastic colon and inflammatory bowel disease), inflammation and scarring.

In another embodiment, inhibition of Syk kinase would be expected to be useful in treating, inhibiting, and/or preventing diseases that are characterized by, caused by and/or associated with autoimmune diseases and/or symptoms of such diseases. Such autoimmune diseases include, but are not limited to, those autoimmune diseases that are frequently designated as single organ or single cell-type autoimmune disorders and those autoimmune diseases that are frequently designated as systemic autoimmune disorders. Non-limiting examples of diseases frequently designated as single organ or single cell-type autoimmune disorders include: Hashimoto's thyroiditis, autoimmune hemolytic anemia, autoimmune atrophic gastritis of pernicious anemia, autoimmune encephalomyelitis, autoimmune orchitis, Goodpasture's disease, autoimmune thrombocytopenia (including immune thrombocytopenia purpura), sympathetic ophthalmia, myasthenia gravis, Graves' disease, primary biliary cirrhosis, chronic aggressive hepatitis, ulcerative colitis and membranous glomerulopathy. Non-limiting examples of diseases often designated as systemic autoimmune disorder include: systemic lupus erythematosis, rheumatoid arthritis, Sjogren's syndrome, Reiter's syndrome, polymyositis-dermatomyositis, systemic sclerosis, polyarteritis nodosa, multiple sclerosis and bullous pemphigoid. Additional autoimmune diseases, which can be B cell (humoral) or T-cell based, include autoimmune alopecia, Type I or juvenile onset diabetes, and thyroiditis.

Inhibition of JAK kinase is expected to be useful in treating, inhibiting, and/or preventing diseases that are characterized by, caused by and/or associated with signaling cascades of cytokine receptors that involve the common gamma chain, such as, for example, the IL-4, IL-7, IL-5, IL-9, IL-15 and IL-21, or IL-2, IL-4, IL-7, 1L-9, IL-15 and IL-21 receptor signaling cascades. Such diseases include, by way of example and not limitation, allergies, asthma, autoimmune diseases such as transplant rejection (e.g., kidney, heart, lung, liver, pancreas, skin; host versus graft reaction (HVGR), etc.), rheumatoid arthritis, and amyotrophic lateral sclerosis, T-cell mediated autoimmune diseases such as multiple sclerosis, psoriasis and Sjogren's syndrome, Type II inflammatory diseases such as vascular inflammation (including vasculitis, arteritis, atherosclerosis and coronary artery disease), diseases of the central nervous system such as stroke, pulmonary diseases such as bronchitis obliteraus and primary pulmonary hypertension, and solid, delayed Type IV hypersensitivity reactions, and hematologic malignancies such as leukemia and lymphomas.

Inhibition of Ax1 kinase is expected to be useful in treating, inhibiting, and/or preventing diseases that are characterized by, caused by and/or associated with apoptosis induced by serum starvation, TNF-α or the viral protein E1A, as well as migration and cell differentiation. Such diseases include, by way of example and not limitation, solid tumors, including, but not limited to, breast, renal, endometrial, ovarian, thyroid, non-small cell lung carcinoma and uveal melanoma; liquid tumors, including but not limited to, leukemias (particularly myeloid leukemias) and lymphomas; endometriosis, vascular disease/injury (including but not limited to restenosis, atherosclerosis and thrombosis), psoriasis; visual impairment due to macular degeneration; diabetic retinopathy and retinopathy of prematurity; kidney disease (including but not limited to glomerulonephritis, diabetic nephropathy and renal transplant rejection), rheumatoid arthritis; osteoarthritis and cataracts.

In yet another aspect of the invention, a method for the treatment or lessening the severity of a proliferative disorder, a cardiac disorder, a neurodegenerative disorder, a psychotic disorder, an autoimmune disorder, a condition associated with organ transplant, an inflammatory disorder, an immunologically mediated disorder, a viral disease, or a bone disorder is provided comprising administering an effective amount of a compound, or a pharmaceutically acceptable composition comprising a compound to a subject in need thereof. In certain embodiments of the present invention an "effective amount" of the compound or pharmaceutically acceptable composition is that amount effective for preventing or delaying the onset, or treating or lessening the severity, of a proliferative disorder, a cardiac disorder, a neurodegenerative disorder, a psychotic disorder, an autoimmune disorder, a condition associated with organ transplant, an inflammatory disorder, an immunologically mediated disorder, a viral disease, or a bone disorder. The compounds and compositions, according to the method of the present invention, may be administered using any amount and any route of administration effective for preventing, delaying the onset, treating or lessening the severity of a proliferative disorder, a cardiac disorder, a neurodegenerative disorder, an autoimmune disorder, a condition associated with organ transplant, an inflammatory disorder, an immunologically mediated disorder, a viral disease, or a bone disorder. The exact amount required will vary from subject to subject, depending on the species, age, and general condition of the subject, the severity of the infection, the particular agent, its mode of administration, and the like.

The compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment and approval by the FDA. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts. The term "patient", as used herein, means an animal, preferably a mammal, and most preferably a human.

The pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the condition being treated. Dosage amounts will typically be in the range of from about 0.0001 or 0.001 or 0.01 mg/kg/day to about 100 mg/kg/day. In certain embodiments, the compounds of the invention may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

As described generally above, the compounds of the invention are useful as inhibitors of protein kinases. In one embodiment, the compounds and compositions of the invention are inhibitors of one or more of SYK, PRAK, GSK3, ERK2, CDK2, MK2, SRC, or Aurora-2 kinase, and thus, without wishing to be bound by any particular theory, the compounds and compositions are particularly useful for treating or lessening the severity of a disease, condition, or disorder where activation of one or more of PRAK, GSK3, ERK2, CDK2, MK2, SRC, SYK, or Aurora-2 kinase is implicated in the disease, condition, or disorder. When activation of PRAK, GSK3, ERK2, CDK2, MK2, SRC, SYK, or Aurora-2 kinase is implicated in a particular disease, condition, or disorder, the disease, condition, or disorder may also be referred to as "PRAK, GSK3, ERK2, CDK2, MK2, SRC, SYK, or Aurora-2 kinase-mediated disease" or disease symptom. Accordingly, in another aspect, the present invention provides a method for treating or lessening the severity of a disease, condition, or disorder where activation or one or more of PRAK, GSK3, ERK2, CDK2, MK2, SRC, SYK, or Aurora-2 kinase is implicated in the disease state.

The activity of a compound utilized in this invention as an inhibitor of PRAK, GSK3, ERK2, CDK2, MK2, SRC, SYK, or Aurora-2 kinase, may be assayed in vitro, in vivo or in a cell line. In vitro assays include assays that determine inhibition of either the phosphorylation activity or ATPase activity of activated PRAK, GSK3, ERK2, CDK2, MK2, SRC, SYK, or Aurora-2 kinase. Alternate in vitro assays quantitate the ability of the inhibitor to bind to PRAK, GSK3, ERK2, CDK2, MK2, SRC, SYK, or Aurora-2 kinase. Inhibitor binding may be measured by radiolabeling the inhibitor prior to binding, isolating the inhibitor/PRAK, inhibitor/GSK3, inhibitor/ERK2, inhibitor/CDK2, inhibitor/MK2, inhibitor/SRC, inhibitor/SYK, or inhibitor/Aurora-2 kinase complex and determining the amount of radiolabel bound. Alternatively, inhibitor binding may be determined by running a competition experiment where new inhibitors are incubated with PRAK, GSK3, ERK2, CDK2, MK2, SRC, SYK, or Aurora-2 kinase bound to known radioligands.

The term "measurably inhibit", as used herein means a measurable change in PRAK, GSK3, ERK2, CDK2, MK2, SRC, SYK, or Aurora-2 kinase activity between a sample comprising said composition and a PRAK, GSK3, ERK2, CDK2, MK2, SRC, SYK, or Aurora-2 kinase kinase and an equivalent sample comprising PRAK, GSK3, ERK2, CDK2, MK2, SRC, SYK, or Aurora-2 kinase kinase in the absence of said composition.

The term "Aurora-2-mediated disease" or "Aurora-2-mediated condition", as used herein, means any disease or other deleterious condition in which Aurora is known to play a role. The terms "Aurora-2-mediated disease" or "Aurora-2-mediated condition" also mean those diseases or conditions that are alleviated by treatment with an Aurora-2 inhibitor. Such conditions include, without limitation, colon, breast, stomach, and ovarian cancer.

The terms "ERK-mediated disease" or "ERK-mediated condition", as used herein mean any disease or other deleterious condition in which ERK is known to play a role. The terms "ERK-2-mediated disease" or "ERK-2-mediated condition" also mean those diseases or conditions that are alleviated by treatment with an ERK-2 inhibitor. Such conditions include, without limitation, cancer, stroke, diabetes, hepatomegaly, cardiovascular disease including cardiomegaly, Alzheimer's disease, cystic fibrosis, viral disease, autoimmune diseases, atherosclerosis, restenosis, psoriasis, allergic disorders including asthma, inflammation, neurological disorders, and hormone-related diseases. The term "cancer" includes, but is not limited to the following cancers: breast, ovary, cervix, prostate, testis, genitourinary tract, esophagus, larynx, glioblastoma, neuroblastoma, stomach, skin, keratoacanthoma, lung, epidermoid carcinoma, large cell carcinoma, small cell carcinoma, lung adenocarcinoma, bone, colon, adenoma, pancreas, adenocarcinoma, thyroid, follicular carcinoma, undifferentiated carcinoma, papillary carcinoma, seminoma, melanoma, sarcoma, bladder carcinoma, liver carcinoma and biliary passages, kidney carcinoma, myeloid disorders, lymphoid disorders, Hodgkin's, hairy cells, buccal cavity and pharynx (oral), lip, tongue, mouth, pharynx, small intestine, colon-rectum, large intestine, rectum, brain and central nervous system, and leukemia. ERK-2 protein kinase and its implication in various diseases has been described (Bokemeyer et al., Kidney Int. 1996, 49, 1187; Anderson et al., Nature 1990, 343, 651; Crews et al., Science 1992, 258, 478; Bjorbaek et al., J. Biol. Chem. 1995, 270, 18848; Rouse et al., Cell 1994, 78, 1027; Raingeaud et al., Mol. Cell Biol. 1996, 16, 1247; Chen et al., Proc. Natl. Acad. Sci. USA 1993, 90, 10952; Oliver et al., Proc. Soc. Exp. Biol. Med. 1995, 210, 162; Moodie et al., Science 1993, 260, 1658; Frey and Mulder, Cancer Res. 1997, 57, 628; Sivaraman et al., J. Clin. Invest. 1997, 99, 1478; Whelchel et al., Am. J. Respir. Cell Mol. Biol. 1997, 16, 589).

The term "GSK-3-mediated disease" as used herein, means any disease or other deleterious condition or disease in which GSK-3 is known to play a role. Such diseases or conditions include, without limitation, autoimmune diseases, inflammatory diseases, metabolic, neurological and neurodegenerative diseases (e.g., Alzheimer's disease, Huntington's disease, Parkinson's disease and basal ganglia movement disorders, chorea, dystonia, Wilson Disease, Pick Disease, frontal lobe degeneration, progessive supranuclear palsy (PSP), Creutzfeldt-Jakob Disease, taupathology and corticobasal degeneration (CBD)), psychotic disorders (e.g., schizophrenia, AIDS-associated dementia, depression, bipolar disorder, and anxiety disorders), cardiovascular diseases, allergy, asthma, diabetes, amyotrophic lateral sclerosis (AML, Lou Gehrig's disease), multiple sclerosis (MS), cardiomyocyte hypertrophy, reperfusion/ischemia, stroke, and baldness.

The term "Src-mediated disease" as used herein means any disease or other deleterious condition in which Src kinase plays a role. Such diseases or conditions include, without limitation, cancers such as colon, breast, hepatic and pancreatic cancer, autoimmune diseases such as transplant rejection, allergies, rheumatoid arthritis, leukemia, bone remodeling diseases such as osteoporosis and viral diseases such as hepatitus B infection.

The terms "CDK-2-mediated disease" or "CDK-2-mediated condition", as used herein, mean any disease or other deleterious condition in which CDK-2 is known to play a role. The terms "CDK-2-mediated disease" or "CDK-2-mediated condition" also mean those diseases or conditions that are alleviated by treatment with a CDK-2 inhibitor. Such conditions include, without limitation, cancer, Alzheimer's disease, restenosis, angiogenesis, glomerulonephritis, cytomegalovirus, HIV, herpes, psoriasis, atherosclerosis, alopecia, and autoimmune diseases such as rheumatoid arthritis. See Fischer, P. M. and Lane, D. P., Current Medicinal Chemistry, 7, 1213 1245 (2000); Mani, S., Wang, C., Wu, K., Francis, R. and Pestell, R., Exp. Opin. Invest. Drugs, 9, 1849 (2000); Fry, D. W. and Garrett, M. D., Current Opinion in Oncologic, Endocrine & Metabolic Investigational Drugs, 2, 40 59 (2000).

The terms "PRAK-mediated disease" or "PRAK-mediated condition", as used herein mean any disease or other deleterious condition in which PRAK is known to play a role. The terms "PRAK-mediated disease" or "PRAK-mediated condition" also mean those diseases or conditions that are alleviated by treatment with a PRAK inhibitor. Such conditions include, without limitation, rheumatoid arthritis, multiple sclerosis (see Darlington, C. L, Current Opinion in Anti-inflammatory & Immunomodulatory Investigational Drugs, 1999, 1 (3),190 198), Crohns Disease, autoimmune diseases, atherosclerosis, restenosis, psoriasis, allergic disorders including asthma, and inflammation.

The term "Syk-mediated disease" or "Syk-mediated condition", as used herein, means any disease or other deleterious condition in which Syk protein kinase is known to play a role. Such conditions include, without limitation, auto-immune, allergic and other disorders described in 0093, 0094, and 0095.

The term "MK2-mediated disease" or "MK2-mediated condition", as used herein, means any disease or other deleterious condition in which MK2 protein kinase is known to play a role. Such conditions include, without limitation, inflammatory disorders, arthritis, ischemia/reperfusion (see, J. Biol. Chem. 2002, 277 (46), 43968 72), and asthma (See., Am J Respir Crit Care Med. 2001 Dec. 1;164(11):2051 6).

In other embodiments, the invention relates to a method of enhancing glycogen synthesis and/or lowering blood levels of glucose in a patient in need thereof, comprising administering to said patient a therapeutically effective amount of a composition of the invention. This method is especially useful for diabetic patients.

In yet another embodiment, the invention relates to a method of inhibiting the production of hyperphosphorylated Tau protein in a patient in need thereof, comprising administering to said patient a therapeutically effective amount of a composition of the invention. This method is especially useful in halting or slowing the progression of Alzheimer's disease.

In still another embodiments, the invention relates to a method of inhibiting the phosphorylation of β-catenin in a patient in need thereof, comprising administering to said patient a therapeutically effective amount of a composition of the invention. This method is especially useful for treating schizophrenia.

It will also be appreciated that the compounds and pharmaceutically acceptable compositions of the present invention can be employed in combination therapies, that is, the compounds and pharmaceutically acceptable compositions can be administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, an inventive compound may be administered concurrently with another agent used to treat the same disorder), or they may achieve different effects (e.g., control of any adverse effects). As used herein, additional therapeutic agents that are normally administered to treat or prevent a particular disease, or condition, are known as "appropriate for the disease, or condition, being treated".

Chemotherapeutic agents or other anti-proliferative agents may be combined with the compounds of this invention to treat proliferative diseases and cancer. For example, other therapies or anticancer agents that may be used in combination with the inventive anticancer agents of the present invention include surgery, radiotherapy (in but a few examples, gamma.-radiation, neutron beam radiotherapy, electron beam radiotherapy, proton therapy, brachytherapy, and systemic radioactive isotopes, to name a few), endocrine therapy, biologic response modifiers (for example, interferons and/or interleukins), hyperthermia and cryotherapy, agents to attenuate any adverse effects (e.g., antiemetics), and other approved chemotherapeutic drugs, including, but not limited to, alkylating drugs (mechlorethamine, chlorambucil, Cyclophosphamide, Melphalan, Ifosfamide), antimetabolites (Methotrexate), purine antagonists and pyrimidine antagonists (6-Mercaptopurine, 5-Fluorouracil, Cytarabile, Gemcitabine), spindle poisons (Vinblastine, Vincristine, Vinorelbine, Paclitaxel), podophyllotoxins (Etoposide, Irinotecan, Topotecan), antibiotics (Doxorubicin, Bleomycin, Mitomycin), nitrosoureas (Carmustine, Lomustine), inorganic ions (Cisplatin, Carboplatin), enzymes (Asparaginase), and hormones (Tamoxifen, Leuprolide, Flutamide, and Megestrol), Gleevec®, adriamycin, dexamethasone, and cyclophosphamide. For a more comprehensive discussion of updated cancer therapies see, www.nci.nih.gov, a list of the FDA approved oncology drugs at www.fda.gov/cder/cancer/druglistframe.htm, and The Merck Manual, Seventeenth Ed. 1999.

Other examples of agents the inhibitors of this invention may also be combined with include, without limitation: treatments for Alzheimer's Disease such as Aricept® and Excelon®; treatments for Parkinson's Disease such as L-DOPA/carbidopa, entacapone, ropinrole, pramipexole, bromocriptine, pergolide, trihexephendyl, and amantadine; agents for treating Multiple Sclerosis (MS) such as β interferon (e.g., Avonex® and Rebif®), Copaxone®, and mitoxantrone; treatments for asthma such as albuterol and Singulair®; agents for treating schizophrenia such as zyprexa, risperdal, seroquel, and haloperidol; anti-inflammatory agents such as corticosteroids, TNF blockers, IL-1 RA, azathioprine, cyclophosphamide, and sulfasalazine; immunomodulatory and immunosuppressive agents such as cyclosporin, tacrolimus, rapamycin, mycophenolate mofetil, interferons, corticosteroids, cyclophosphamide, azathioprine, and sulfasalazine; neurotrophic factors such as acetylcholinesterase inhibitors, MAO inhibitors, interferons, anti-convulsants, ion channel blockers, riluzole, and anti-Parkinsonian agents; agents for treating cardiovascular disease such as β-blockers, ACE inhibitors, diuretics, nitrates, calcium channel blockers, and statins; agents for treating liver disease such as corticosteroids, cholestyramine, interferons, and anti-viral agents; agents for treating blood disorders such as corticosteroids, anti-leukemic agents, and growth factors; and agents for treating immunodeficiency disorders such as gamma globulin.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

The compounds of this invention or pharmaceutically acceptable compositions thereof may also be incorporated into compositions for coating implantable medical devices, such as prostheses, artificial valves, vascular grafts, stents and catheters. Accordingly, the present invention, in another aspect, includes a composition for coating an implantable device comprising a compound of the present invention as described generally above, and in classes and subclasses herein, and a carrier suitable for coating said implantable device. In still another aspect, the present invention includes an implantable device coated with a composition comprising a compound of the present invention as described generally above, and in classes and subclasses herein, and a carrier suitable for coating said implantable device.

Vascular stents, for example, have been used to overcome restenosis (re-narrowing of the vessel wall after injury). However, patients using stents or other implantable devices risk clot formation or platelet activation. These unwanted effects may be prevented or mitigated by pre-coating the device with a pharmaceutically acceptable composition comprising a kinase inhibitor. Suitable coatings and the general preparation of coated implantable devices are described in U.S. Pat. Nos. 6,099,562; 5,886,026; and 5,304,121. The coatings are typically biocompatible polymeric materials such as a hydrogel polymer, polymethyldisiloxane, polycaprolactone, polyethylene glycol, polylactic acid, ethylene vinyl acetate, and mixtures thereof. The coatings may optionally be further covered by a suitable topcoat of fluorosilicone, polysaccarides, polyethylene glycol, phospholipids or combinations thereof to impart controlled release characteristics in the composition.

Another aspect of the invention relates to inhibiting PRAK, GSK3, ERK2, CDK2, MK2, SRC, SYK, or Aurora-2 kinase activity in a biological sample or a patient, which method comprises administering to the patient, or contacting said biological sample with a compound of formula I or a composition comprising said compound. The term "biological sample", as used herein, includes, without limitation, cell cultures or extracts thereof; biopsied material obtained from a mammal or extracts thereof; and blood, saliva, urine, feces, semen, tears, or other body fluids or extracts thereof.

Inhibition of PRAK, GSK3, ERK2, CDK2, MK2, SRC, SYK, or Aurora-2 kinase kinase activity in a biological sample is useful for a variety of purposes that are known to one of skill in the art. Examples of such purposes include, but are not limited to, blood transfusion, organ-transplantation, biological specimen storage, and biological assays.

Other aspects of the invention include, but are not limited to, intermediates and methods useful for synthesizing the stereoisomerically enriched compounds and prodrugs, as described herein.

In Vivo Test Procedures for SYK Inhibitors

In yet another aspect of the invention, a method for screening for SYK-inhibiting compounds is provided.

The invention will be illustrated in more detail with reference to the following Examples, but it should be understood that the present invention is not deemed to be limited thereto.

EXAMPLES

Inhibitors of Syk kinase can be screened from a compound library in an in vitro Syk kinase reaction using poly GluTyr as the substrate. Reactions can be quantified by measuring ATP used by the kinase in a luciferase reporter assay. In this assay, purified Syk kinase is mixed with potential inhibitor compound in the presence of ATP and poly GluTyr substrate. After the kinase reaction, remaining ATP is detected by adding luciferin and luciferase. In the presence of ATP, luciferrin is oxidized by luciferase to produce oxyluciferin and light. The light is quantitated and corresponds to the amount of ATP remaining from the original reaction. In this system, decreased light corresponds to increased kinase activity. Reactions in which compounds inhibited kinase activity will have more ATP remaining and so the light produced will be great.

Inhibitors of Syk kinase were screened from a library of over 100,000 compounds. In order to maximize the potential for finding a viable drug candidate, compounds were chosen for maximum diversity, thereby allowing detection of representatives from the largest number of chemical families. Compounds were screened for the ability to inhibit Syk phosphorylation of the kinase substrate poly GluTyr. Reactions were quantified by measuring ATP usage using a luciferase reporter assay. Of the compounds screened, 342 were active in the primary screen; 101 compounds were confirmed active by retesting the active compounds in quadruplicate. Of the confirmed hits, 9 met the criteria of reproducible dose response curves with IC50 values less than 30 µM.

Assay Development

The Syk kinase assay was optimized for high throughput screening in 384 well plates.

Kinase activity was measured with the Kinase-glo kit (Promega) that detects ATP using the luciferase reporter system.

FIG. 1 shows the assay used to detect activity. Kinases use ATP to phosphorylate a substrate. After incubation of the kinase with substrate and ATP, luciferin and luciferase are added to the assay. In the presence of ATP, luciferin is oxidized by luciferase, and the light produced is quantified on a plate reader. In this assay, increased kinase activity yields decreased light production.

The ATP standard curve produced with the Kinase-glo kit was linear up to 5 µM ATP. A final ATP concentration of 0.5 µM was used for all subsequent screening assays.

Figure 2:
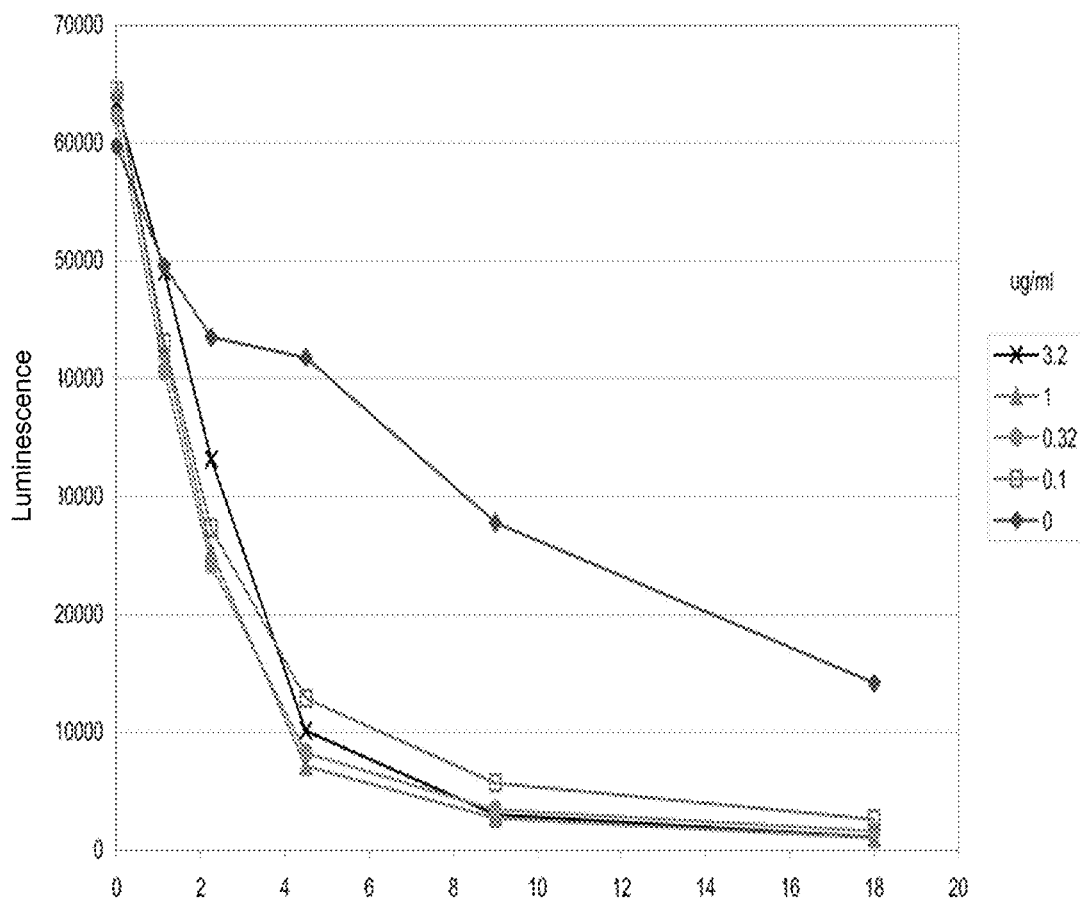
FIG. 2 is a graph of luminescence against enzyme concentration.

The Syk kinase assay was optimized for screening by titrating both syk kinase (Millipore, USA) and the substrate, poly Glu-Tyr (Sigma, St. Louis, Mo.) (FIG. 2). In the absence of substrate, there was significant reduction of ATP most likely due to syk autophosphorylation. Increasing substrate from 0.1 to 3.2 µg/ml poly Glu-Tyr did not increase ATP consumption. Final assay conditions used were 0.32 µg/ml substrate and 9 ng/ml syk kinase.

Staurosporine (Cayman Chemical, Ann Arbor, Mich.), a known syk kinase inhibitor, was used to characterize the assay. Staurosporine showed potent, reproducible inhibition of syk kinase, with an IC50 value of 2.9 nM. Staurosporine was included on every plate in the screening assay, using a high concentration (100 nM) to totally inhibit the syk kinase reaction.

Primary Screen

Based on these data, a screen was conducted using compounds from a compound library. These compounds were chosen for maximum chemical diversity. On each plate, 336 compounds were tested along with 44 uninhibited control samples and 4 inhibited control samples (containing 100 nM staurosporine). Using the TiMo head on the Tecan Freedom EVO robot, 5 µl of test compounds (100 µM compound in assay buffer with 10% DMSO) were dispensed to each of the assay wells of a 384 well microplate. Final concentration of compounds was 25 µM. A 10 ul solution of Syk kinase (9 nM final concentration) was added to the wells, followed by the substrates (5 µl of 2 mM ATP, 1.28 µg/ml poly Glu4Tyr; final concentrations were 0.5 µM and 0.32 µg/ml, respectively). Reactions were incubated for 2 hours at room temperature. Then, 5 µl of Kinase-glo reagent was added for 10 minutes. Luminescence was recorded on a BMG Pherastar reader.

The Kinase-glo assay is an indirect measurement of syk kinase activity as it measures the amount of ATP not used by syk. Consequently, in the absence of inhibition, the amount of light generated is low. Kinase inhibitors reduce consumption of ATP, resulting in increased generation of light. One advantage of this protocol is that compounds that interfere with the luciferase assay and consequent light production are not scored as kinase inhibitors.

Assay performance was assessed by the variability of the control wells. Controls were pooled based on a statistical analysis of similarity of the values. For the uninhibited controls, there were three separate groups. For the inhibited controls, there were two groups. The uninhibited controls values were somewhat variable with the percent coefficient of variation (% CV) all greater than 10%. A cutoff value of 3× the standard deviation of the uninhibited wells (3×SD) was set for each pool group. The 342 active compounds were selected based on these cutoff values.

FIG. 3 shows data from about half of the primary screen. The cutoff value of 3×SD is shown as the solid line. The dashed line represents the staurosporine inhibited control value.

Secondary Screen.

For secondary assays, compounds identified in the primary screen were tested in quadruplicate under the exact same assay conditions, again using 3× the standard deviation of uninhibited control values as the cutoff. Of the original 342 hits, 101 compounds were confirmed active.

Dose Response Assays

Dose response assays were conducted on the 101 confirmed active compounds. These were tested at 11 concentrations, from 0.3 µM to 100 µM. Compounds that gave dose response curves with Hill slopes between 0.5 and 2 were retested in duplicate. Only those compounds exhibiting reproducible dose response curves with IC50 less than 30 uM were to be considered for further development. Nine compounds were identified at the end of the final test.

Syk Inhibition Assay

Inhibition of syk can be determined in a syk dependent cellular assay such as neutrophil respiratory burst, degranulation and phagocytosis.

During the respiratory burst, reactive oxygen intermediates such as superoxide anion, hydroxyl radical, and hydrogen peroxide are produced. To determine the ability of an inhibitor of syk to inhibit respiratory burst, superoxide anion production can be measured in a microplate assay using the reduction of cytochrome c as a reporter assay.

Neutrophils (1×10$^5$) can be added to microtiter plates previously coated with fibrinogen. Samples can be equilibrated at 37° C. and the reaction initiated by adding 20 ng/ml TNFα. Reduction of cytochrome c can be quantified by measuring absorbance at 550 nm using a microplate reader. Inhibition of respiratory burst will be indicated by a decrease in cytochrome c reduction in comparison to the positive control.

The ability of inhibitors to inhibit degranulation can be assessed by measuring lactoferrin, a secondary granule product using an enzyme linked immunosorbant assay (ELISA). Neutrophils plated into fibrinogen coated wells of a microtiter plate can be stimulated with 20 ng/ml TNFα in the presence of syk inhibitors. After appropriate times, supernatants can be tested for lactoferrin. In this assay, lactoferrin from the supernatant is captured by a monoclonal antibody (MAb) that is coated on wells of a sectional microplate. A second LTF-MAb labeled with biotin is added to the well and binds with the captured LTF forming a "sandwich." A solution of streptavidin-peroxidase is then added. Streptavidin has a high affinity for biotin and once bound, its horseradish peroxidase (HRP) label is available for color development by addition of the substrate, o-phenylenediamine (OPD). This color development at 450 nm is proportional to the quantity of lactoferrin in the sample. Assays will be quantified in a microplate reader at 450 nm.

Inhibition of phagocytosis can be carried out using the CytoSelect™ 96-Well

Phagocytosis Assay (Cell Biolabs, Inc). The phagocytic target is Zymosan (*Saccharomyces cerevisiae*), made from yeast cell wall and is composed of a mixture of protein and carbohydrates. For this assay, neutrophils can be seeded onto fibrinogen coated wells in the presence of inhibitor. Zymosan is added for varying times, and phagocytosis detected by permeabilizing the cells and adding a detection reagent that can be quantified colorimetrically in a plate reader at 405 nm.

Compounds of the invention may be found to inhibit SYK. In certain embodiments, compounds may be shown to have $K_i$ values less than 1.0 µM for SYK.

While the invention has been described in detail and with reference to specific examples thereof, it will be apparent to one skilled in the art that various changes and modifications can be made therein without departing from the spirit and scope thereof.

What is claimed is:

1. A pharmaceutical composition comprising the compound

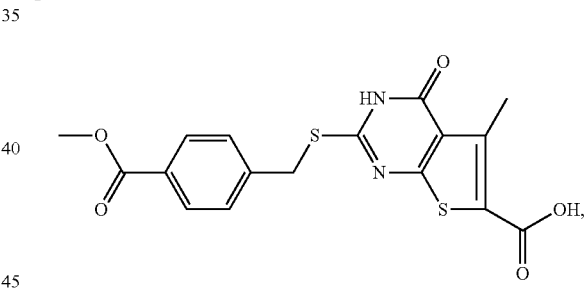

polymorphs thereof, salts thereof, hydrates thereof, and solvates thereof and at least one of a pharmaceutically acceptable carrier, a diluent and an excipient, wherein the composition is in the form of lozenges, tablets, films or capsules.

2. A method of inhibiting a Syk kinase in an animal, comprising the step of administering to the animal an amount of a composition of claim 1 effective to inhibit a Syk kinase.

3. The method of claim 2, wherein the animal is a human.

* * * * *

UNITED STATES PATENT AND TRADEMARK OFFICE
CERTIFICATE OF CORRECTION

| | |
|---|---|
| PATENT NO. | : 8,389,525 B2 |
| APPLICATION NO. | : 12/774230 |
| DATED | : March 5, 2013 |
| INVENTOR(S) | : Desai et al. |

It is certified that error appears in the above-identified patent and that said Letters Patent is hereby corrected as shown below:

In the Specifications:

At col. 18, lines 23-27:
"Initial dosages may also be estimated from in vivo data, such as animal models. Animal models useful for testing the efficacy of compounds to treat or prevent the various diseases described above are well-known in the art."
should be
--Initial dosages may also be estimated from in vivo data, such as animal models. Animal models useful for testing the efficacy of compounds to treat or prevent the various diseases described above are well-known in the art.--

At col. 20, line 8:
"...IKK-2 (=HOC-β)..."
should be
--...IKK-2 (IKK-β)...--

At col. 23, lines 42-49:
"The term "measurably inhibit", as used herein means a measurable change in PRAK, GSK3, ERK2, CDK2, MK2, SRC, SYK, or Aurora-2 kinase activity between a sample comprising said composition and a PRAK, GSK3, ERK2, CDK2, MK2, SRC, SYK, or Aurora-2 kinase kinase and an equivalent sample comprising PRAK, GSK3, ERK2, CDK2, MK2, SRC, SYK, or Aurora-2 kinase kinase in the absence of said composition."
should be
--The term "measurably inhibit", as used herein means a measurable change in PRAK, GSK3, ERK2, CDK2, MK2, SRC, SYK, or Aurora-2 kinase activity between a sample comprising said composition and a PRAK, GSK3, ERK2, CDK2, MK2, SRC, SYK, or Aurora-2 kinase and an equivalent sample comprising PRAK, GSK3, ERK2, CDK2, MK2, SRC, SYK, or Aurora-2 kinase in the absence of said composition.--

Signed and Sealed this
Eleventh Day of June, 2013

Teresa Stanek Rea
*Acting Director of the United States Patent and Trademark Office*